United States Patent [19]

Kim

[11] Patent Number: 4,751,072

[45] Date of Patent: Jun. 14, 1988

[54] METHOD OF DESENSITIZING HYPERSENSITIVE DENTIN EMPLOYING COMPOSITIONS CONTAINING POTASSIUM CHLORIDE

[75] Inventor: Syngcuk Kim, Orangeburg, N.Y.

[73] Assignee: The Trustees of Columbia University in the City of New York, New York, N.Y.

[21] Appl. No.: 851,257

[22] Filed: Apr. 14, 1986

Related U.S. Application Data

[62] Division of Ser. No. 589,163, Mar. 13, 1986, Pat. No. 4,631,185.

[51] Int. Cl.⁴ .................................................. A61K 7/16
[52] U.S. Cl. ......................................... 424/49; 424/153
[58] Field of Search ........................... 424/49, 153, 435

[56] References Cited

U.S. PATENT DOCUMENTS

| | | | |
|---|---|---|---|
| 380,700 | 4/1888 | Schwartz | 424/153 |
| 420,186 | 1/1890 | Clark | 424/153 |
| 1,551,638 | 9/1925 | Brady | 424/153 |
| 3,337,404 | 8/1967 | Polli et al. | 424/153 |
| 3,689,636 | 9/1972 | Svajda | 424/49 |
| 3,863,006 | 1/1975 | Hodosh | 424/49 |
| 4,057,621 | 11/1977 | Pashley et al. | |
| 4,327,079 | 4/1982 | Aoki | 424/49 X |

OTHER PUBLICATIONS

*Accepted Dental Remedies*, Seventh Edition, p. 187 (1941).

*Primary Examiner*—Nancy A. B. Swisher
*Attorney, Agent, or Firm*—John P. White

[57] ABSTRACT

A method for reducing sensory nerve activity in a hypersensitive tooth and for desensitizing hypersensitive dentin involves applying to the surface of exposed dentin of a subject's tooth a potassium salt selected from the group consisting of potassium bicarbonate and potassium chloride in an amount effective to reduce sensory nerve activity and to desensitize hypersensitive dentin of hypersensitive teeth.

In the presently preferred embodiment of the invention, potassium bicarbonate is the potassium salt and is applied in a formulation, for example, an aqueous solution containing from about 1.0 to about 360.0 mg of potassium bicarbonate per ml of solution.

10 Claims, 4 Drawing Sheets

FIGURE I
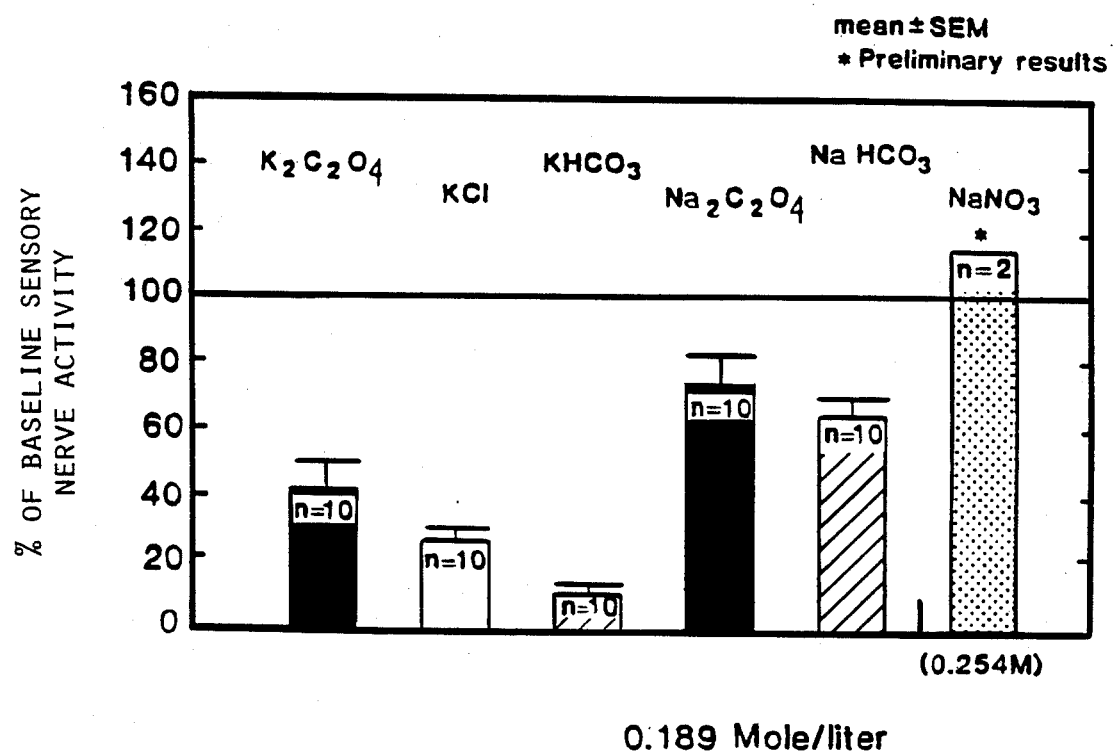

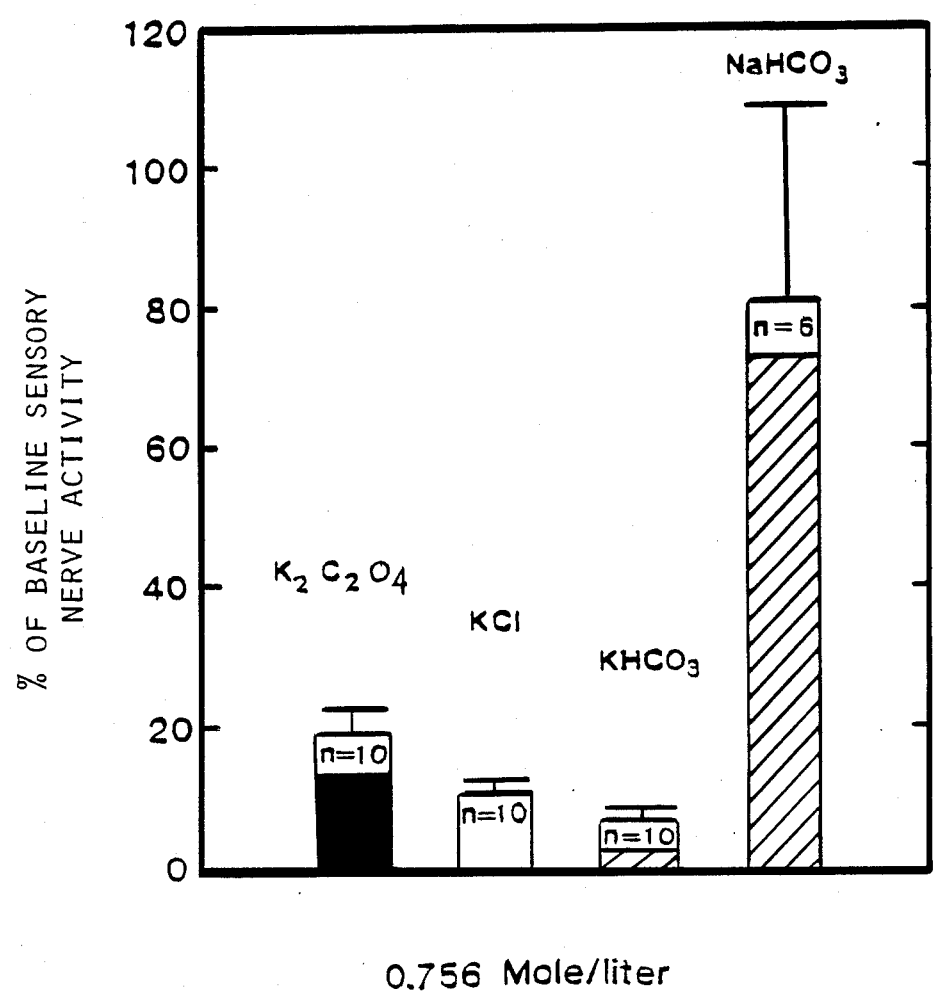
FIGURE II

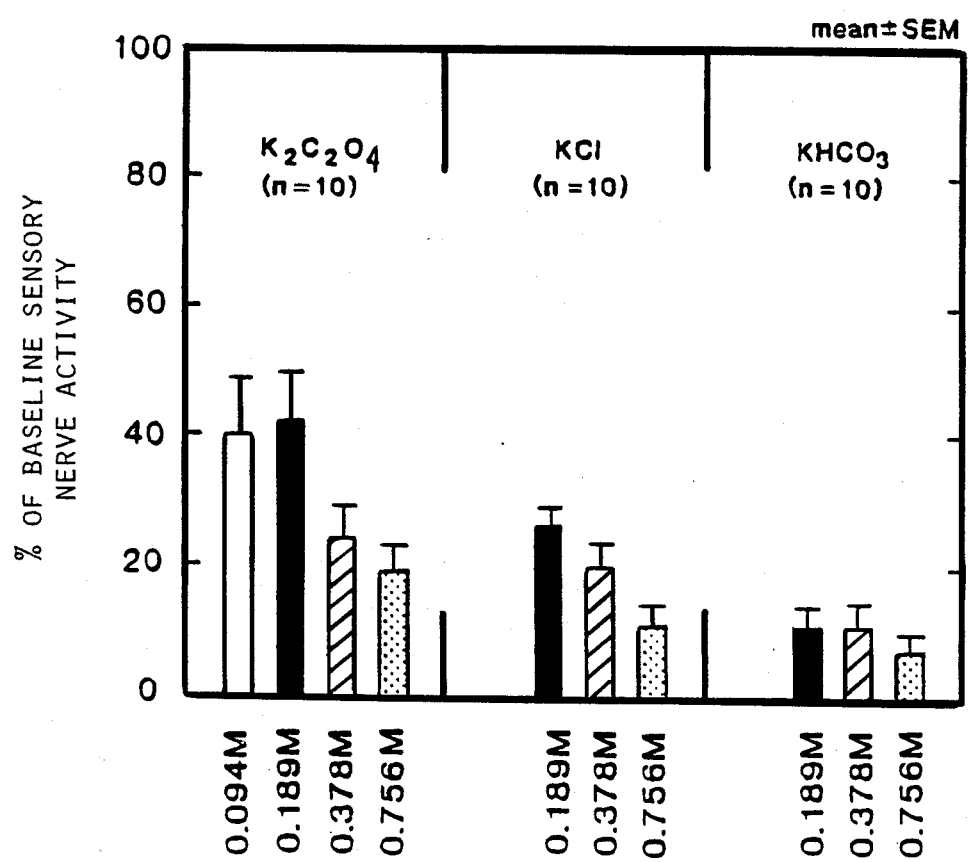
FIGURE III

FIGURE IV
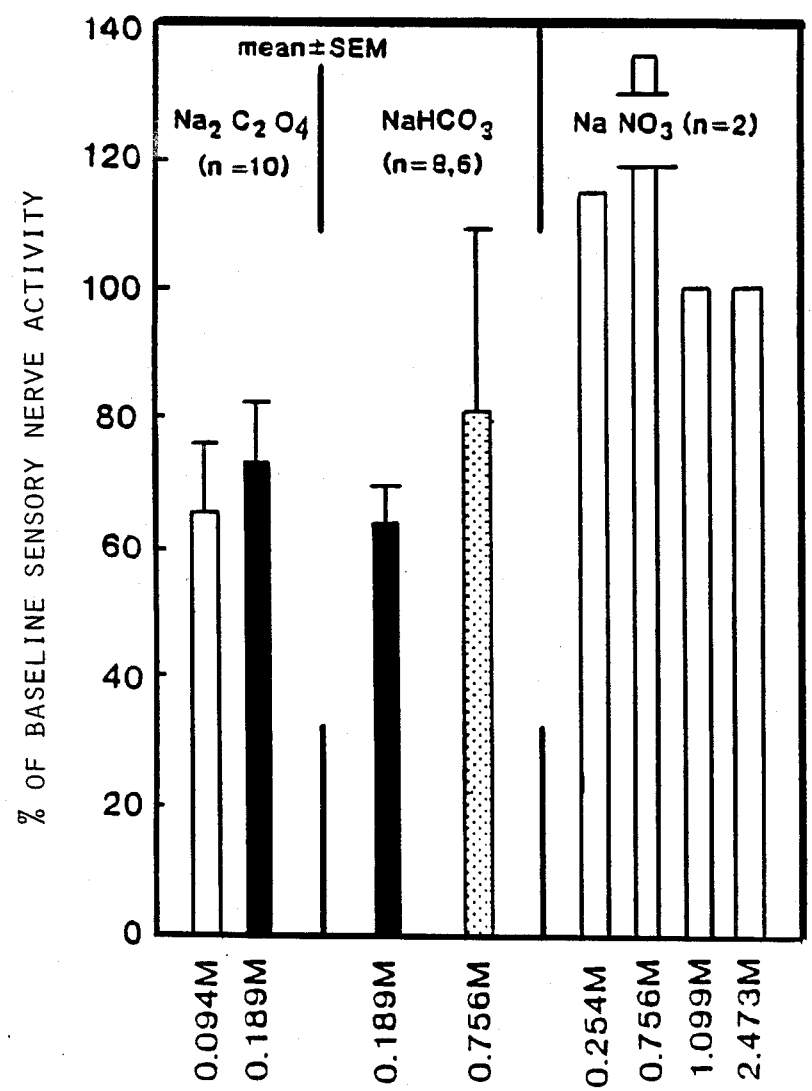

4,751,072

METHOD OF DESENSITIZING HYPERSENSITIVE DENTIN EMPLOYING COMPOSITIONS CONTAINING POTASSIUM CHLORIDE

This ia a division of application U.S. Ser. No. 589,163, filed Mar. 13, 1984, now patented as U.S. Pat. No. 4,631,185.

BACKGROUND OF THE INVENTION

The sensory nerves of the teeth are subject to stimuli from various sources, including heat, cold, sugars, hypertonic solutions and the like. Usually, these various stimuli do not disturb the normal functioning of the dental sensory nerves. However, when the sensory nerves become more easily excitable, for example, because of dental erosion, gum recession, exposure of the dentin or other causes, the teeth are more sensitive than usual to stimuli, resulting in distress and pain. When such an elevation of sensory nerve activity occurs, it is necessary to reduce the dental sensory nerve activity and to desensitize the hypersensitive dentin in order to reduce or relieve the pain. One way of accomplishing this result is to apply to the dentin an effective amount of a substance which can reduce sensory nerve activity and desensitize the hypersensitive dentin.

Numerous methods for desensitizing hypersensitive teeth have been described and a number of commercial products exist for this purpose. However, none of these methods involve the potassium salts of the present invention.

A composition containing a mixture of 12.5 grams of potassium carbonate and 2.5 grams of anhydrous sodium carbonate has been described as useful for the treatment of hypersensitive dentin, *Accepted Dental Remedies*, Seventh Edition, page 187 (1941). Hodosh, U.S. Pat. No. 3,863,006 (1975) discloses the use of nitrate salts, including potassium nitrate, for desensitizing hypersensitive teeth and dentin. Hodosh also discloses that other potassium salts were tried but none were as effective as the nitrate (col. 1, lines 62–64). Pashley, et al., U.S. Pat. No. 4,057,621 (1977) disclose the use of compositions containing oxalate salts, including potassium oxalate, for desensitizing hypersensitive dentin and teeth. Svajda, U.S. Pat. No. 3,689,636 (1972) discloses the use of compositions for desensitizing sensitive teeth containing a mixture of chloride salts of calcium, magnesium, sodium and potassium, preferably each being present in equal parts of saturated aqueous solutions. However, Svajda neither teaches or suggests that any one component of the mixture may be employed alone or that any one component provides greater desensitizing action than another component. Specifically, Svajda neither teaches or suggests that potassium chloride is particularly useful for desensitizing sensitive teeth and dentin.

It has now been unexpectedly found that the application of potassium bicarbonate or potassium chloride in effective amounts to the surface of the dentin of a subject's hypersensitive teeth reduces sensory nerve activity and desensitizes hypersensitive dentin to a degree not previously achieved with other methods of treatment. When applied at equal concentrations potassium bicarbonate, in particular, yields better results than other sensory nerve activity inhibitors or dentin desensitizers.

SUMMARY OF THE INVENTION

This invention concerns a method for reducing sensory nerve activity in hypersensitive teeth and for desensitizing hypersensitive dentin. The method involves applying to the surface of exposed dentin of a subject's hypersensitive teeth a potassium salt selected from the group consisting of potassium bicarbonate and potassium chloride in an amount effective to reduce sensory nerve activity and to desensitize hypersensitive dentin. The potassium salt will typically be applied as part of a formulation, for example, a dentifrice, an aqueous solution, a mouthwash or a chewing gum.

In the presently preferred embodiment of the invention, potassium bicarbonate is the potassium salt applied to the dentin of the subject's hypersensitive teeth, for example, in an aqueous solution wherein the amount of potassium bicarbonate is an amount from about 1.0 to about 360.0 mg/ml of solution.

The method may be used to reduce sensory nerve activity resulting from sensitivity of teeth to heat, cold, sugars, hypertonic solutions and the like and to desensitize dentin which has been made hypersensitive to these stimuli. In this way, the pain resulting from stimulation of hypersensitive nerve tissue may be reduced or relieved.

BRIEF DESCRIPTION OF THE DRAWINGS

FIGS. I to IV set forth in bar graph form the results of comparative experiments demonstrating the subject invention. In the figures, the frequency of sensory nerve activity in experimental animals (cats) relative to a baseline level for untreated cats is shown. In each case sensory nerve activity elicited by stimulating a dental cavity with 9% NaCl after treatment of the dental cavity with different agents at various concentrations was compared with nerve activity in cats stimulated without prior treatment. Values less than the baseline level, i.e., less than the 100% value assigned to untreated cats indicated that the treatment had a positive result, i.e., reduction of sensory nerve activity.

FIG. I compares the frequency of sensory nerve activity as a percentage of the baseline level when dental cavities were stimulated with 9% NaCl following treatment with potassium oxalate, $K_2C_2O_4$; potassium chloride, KCl; potassium bicarbonate, $KHCO_3$; sodium oxalate, $Na_2C_2O_4$; sodium bicarbonate $NaHCO_3$ and sodium nitrate, $NaNO_3$, each in aqueous solution at a concentration of 0.189 mole/liter and with $NaNO_3$ in aqueous solution at a concentration of 0.254 mole/liter. (n=number of cats tested)

FIG. II compares the frequency of sensory nerve activity as a percentage of the baseline level when dental cavities were stimulated with 9% NaCl following treatment with $K_2C_2O_4$, KCl, $KHCO_3$, and $NaHCO_3$, each at a concentration of 0.756 mole/liter in an aqueous solution.

FIG. III compares the frequency of sensory nerve activity as a percentage of the baseline level when dental cavities were stimulated with 9% NaCl following treatment with $K_2C_2O_4$, KCl, $KHCO_3$, at various concentrations.

FIG. IV shows, for comparative purposes, the frequency of sensory nerve activity as a percentage of the baseline level when dental cavities were stimulated with 9% NaCl following treatment with $Na_2C_2O_4$, $NaHCO_3$ and $NaNO_3$ at various concentrations.

DETAILED DESCRIPTION OF THE INVENTION

An effective amount of a potassium salt selected from the group consisting of potassium bicarbonate and potassium chloride is applied to the surface of exposed dentin of a human subject's hypersensitive tooth to desensitize hypersensitive dentin and to reduce sensory nerve activity of a tooth which is hypersensitive to stimuli such as heat, cold, sugars, hypertonic solutions and the like. Preferably, the potassium salt is potassium bicarbonate. Typically, the potassium salt is applied as part of a formulation such as an aqueous solution, a dentrifice, a mouthwash or a chewing gum. In an aqueous solution the effective concentration of potassium chloride is from about 0.7 mg/ml to about 360 mg/ml. In an aqueous solution the effective concentration of potassium bicarbonate is from about 1.0 mg/ml to about 360 mg/ml. Preferably, the concentration is from about 0.05M to about 2.5M, i.e., about 3.5 to about 185 mg of potassium chloride/ml or about 5 to about 250 mg of potassium bicarbonate/ml.

The potassium salt may be applied to the dentin of the subject's teeth in various formulations, including, for example, a dentifrice, a mouthwash or a chewing gum. Furthermore, such formulations may contain a mixture of both potassium bicarbonate and potassium chloride and may include fillers, excipients, preservative, flavoring agents, coloring agents and the like, all of which are well known for use in dental preparations.

The application of potassium salts, preferably potassium bicarbonate, to the dentin, in accordance with this invention, results in a dramatic decrease in the frequency of sensory nerve activity.

The examples which follow are set forth in order to aid in the understanding of the efficacy of applying potassium bicarbonate or potassium chloride to reduce sensory nerve activity and to desensitize hypersensitive dentin. The examples are not intended, and should not be construed, to limit the invention as defined by the claims which follow thereafter.

EXAMPLE 1

Dentifrice

A decrease in the frequency of sensory nerve activity of a hypersensitive tooth may be obtained by applying to exposed dentin of the hypersensitive tooth a dentifrice having a composition as follows:

|  | Percent by weight |
| --- | --- |
| Potassium bicarbonate or Potassium chloride | 0.1–20.0 |
| Sodium monofluorophosphate | 0.2–3.0 |
| Water | 10.0–50.0 |
| Glycerin | 0.0–30.0 |
| Sorbitol solution | 0.0–30.0 |
| Dicalcium phosphate dihydrate | 5.0–40.0 |
| Dicalcium phosphate anhydrous | 0.5–15.0 |
| Sodium lauryl sulfate | 0.5–2.0 |
| Hydroxyethyl cellulose | 0.5–2.0 |
| Flavoring agent | 0.5–2.0 |
| Silica | 0.1–1.0 |
| Sodium saccharin | 0.005–0.5 |
| Methyl paraben | 0.1–1.0 |
| Propyl paraben | 0.1–1.0 |
| FD&C Blue #1 | 0.0–0.2 |
| FD&C Yellow #10 | 0.0–0.2 |

EXAMPLE 2

Mouthwash

A decrease in the frequency of sensory nerve activity of a hypersensitive tooth may be achieved by applying to exposed dentin of the hypersensitive tooth a mouthwash having a composition as follows:

|  | Percent by weight |
| --- | --- |
| Potassium bicarbonate or potassium chloride | 0.1–20.0 |
| Sodium monofluorophosphate | 0.2–3.0 |
| Alcohol | 2.0–30.0 |
| Glycerin | 2.0–15.0 |
| Sorbitol | 2.0–15.0 |
| Flavor | 0.05–0.8 |
| Polysorbate 60 | 0.5–2.0 |
| Sodium saccharin | 0.05–0.5 |
| Sodium benzoate | 0.05–0.2 |
| FD&C dye | 0.0–1.0 |
| Water | 0.0–100.0 |

EXAMPLE 3

An Acute Model for Recording Sensory Nerve Activity

In order to determine and to record sensory nerve activity in subject animals (cats), the following model was developed.

Following anesthetization with sodium pentobarbital (i.v., 30 mg/kg), and artificial ventilation, two dentinal cavities were prepared as recording cavities on the buccal surface of the tooth. One recording cavity was prepared over the incisal pulp horn, and the other within the gingival part of the crown. A third cavity was prepared on the lingual surface of the incisal cavity into which various desensitizing agents were placed. Low impedance platinum electrodes were placed in each of the two recording cavities in contact with exposed dentin, and the recording cavities were filled with a solution of isotonic saline. The recording cavities were insulated with silicone paste, to avoid salt bridge formation between the cavities. Electrical potential between the platinum electrodes was amplified for frequency analysis by electrophysiological equipment. The nerve response elicited by applying 9% NaCl hypertonic solution to the third cavity was used to establish baseline activity (i.e., the baseline sensory nerve activity level). In all experiments, a 1 minute application of testing agents was followed by reapplication of the 9% NaCl hypertonic solution. The effect on sensory activity was compared to the baseline sensory nerve activity. A 30 minute interval with frequent saline flushing of the third cavity was permitted between testing different agents to allow for the reestablishment of baseline sensory nerve activity levels.

EXAMPLE 4

Comparative Experiments

In comparative experiments the agents and concentrations tested were as follows: $K_2C_2O_4$ (0.094M, 0.189M, 0.378M, 0.756M); KCl (0.189M, 0.378M, 0.756M); $KHCO_3$ (0.189M, 0.378M, 0.756M); $Na_2C_2O_4$ (0.094M, 0.189M) and $NaHCO_3$ (0.189M, 0.756M).

For each concentration of $K_2C_2O_4$, KCl, $KHCO_3$, and $Na_2C_2O_4$, 10 experimental animals (cats) were used. In the case of $NaHCO_3$, 8 animals were used to 0.189M, 6 at 0.756M. Additionally, the following agent and concentrations were tested: $NaNO_3$ (0.245M, 0.756M, 1.099M, 2.473M). However, limited data is available on these experiments with $NaNO_3$ since only 2 experimental animals were used.

The results of these experiments are shown in the accompanying bar graphs, FIGS. I, II, III and IV. As will be seen, $KHCO_3$ effects the greatest reduction of sensory nerve impulse at all concentrations studied followed by KCl.

The superiority of $KHCO_3$ and KCl as sensory nerve activity inhibitors is made more clear by setting forth the data of FIGS. I and II in comparative form, i.e., FIGS. III and IV. FIG. III compares the relative levels of sensory nerve impulse activity as a percentage of the baseline sensory nerve activity following treatment with $K_2C_2O_4$, KCl and $KHCO_3$, while FIG. IV includes further data comparing the relative levels of sensory nerve impulse activity following treatment with $Na_2C_2O_4$, $NaHCO_3$ and $NaNO_3$ at various concentrations.

FIG. I shows clearly that at equivalent concentrations, $KHCO_3$ reduces sensory nerve impulse activity better than $K_2C_2O_4$, KCl, $Na_2C_2O_4$, and $NaHCO_3$, and better than $NaNO_3$ even at a greater concentration. FIG. I also shows that KCl is superior at equivalent concentrations to all agents tested except $KHCO_3$. FIG. II shows that $KHCO_3$ continues to show superior results compared to $K_2C_2O_4$, KCl, and $NaHCO_3$ at a concentration of 0.756 mole/liter. FIGS. III and IV show that over a wide range of concentration first $KHCO_3$ and then KCl are the most effective agents for inhibiting sensory nerve activity and desensitizing hypersensitive dentin.

Potassium bicarbonate is thus the preferred agent for desensitizing hypersensitive dentin and for inhibiting elevated sensory nerve activity. Potassium chloride although not quite as effective is nevertheless more effective than any of the other agents tested. One of ordinary skill in the art to which this invention pertains would understand that the model employed may be extended to apply to human beings. At concentrations from about 0.01M to solution saturation potassium bicarbonate and potassium chloride are more effective than other agents when used for desensitizing hypersensitive dentin or reducing sensory nerve activity in hypersensitive teeth.

What is claimed is:

1. A method for reducing sensory nerve activity in a hypersensitive tooth of a subject which comprises applying to the surface of exposed dentin of the hypersensitive tooth a formulation consisting essentially of potassium chloride as the desensitizing agent in an amount effective to reduce the sensory nerve activity of the hypersensitive tooth.

2. A method according to claim 1, wherein the subject is a human being.

3. A method according to claim 1, wherein the formulation is a dentrifice, mouthwash or chewing gum formulation.

4. A method according to claim 1, wherein the formulation is an aqueous solution and the amount of potassium chloride is from about 0.7 mg/ml to about 360 mg/ml of the formulation.

5. A method according to claim 4, wherein the amount is from about 3.5 mg/ml to about 185 mg/ml of the formulation.

6. A method for desensitizing hypersensitive dentin which comprises applying to the surface of exposed dentin a formulation consisting essentially of potassium chloride as the desensitizing agent in an amount effective to reduce the sensory nerve activity of hypersensitive dentin.

7. A method according to claim 6, wherein the subject is a human being.

8. A method according to claim 6, wherein the formulation is a dentrifice, mouthwash or chewing gum formulation.

9. A method according to claim 6, wherein the formulation is an aqueous solution and the amount of potassium chloride is from about 0.7 mg/ml to about 360 mg/ml of the formulation.

10. A method according to claim 9, wherein the amount is from about 3.5 mg/ml to about 185 mg/ml of the formulation.

* * * * *